US00PP07834P

United States Patent [19]

Moser

[11] Patent Number: Plant 7,834

[45] Date of Patent: Mar. 24, 1992

[54] HIBISCUS PLANT NAMED WAIKIKI

[75] Inventor: Frank C. Moser, Alva, Fla.

[73] Assignee: Yoder Brothers, Inc., Barberton, Ohio

[21] Appl. No.: 578,770

[22] Filed: Sep. 7, 1990

[51] Int. Cl.[5] ..... A01H 5/00
[52] U.S. Cl. ..... Plt./54
[58] Field of Search ..... Plt. 54, 68, 67.8

*Primary Examiner*—Howard J. Locker

*Attorney, Agent, or Firm*—Foley & Lardner

[57] ABSTRACT

A Hibiscus plant named Waikiki particularly characterized by its pink flower color with a dark red eye; regular single flower form; flower diameter of 120 to 145 mm; excellent pot habit with vigorous growth, good branching and very uniform performance; flower life of a single day; easy to propagate; good resistance to Bacterial Leaf Spot, (Pseudomonas sp.); and good shipping tolerance.

2 Drawing Sheets

The present invention comprises a new and distinct cultivar of Hibiscus, botanically known as *Hibiscus rosasinensis L.*, and referred to by the cultivar name Waikiki.

Waikiki, identified as 85-157003, was originated from a cross made by Frank C. Moser in a controlled breeding program in Alva, Fla., in 1984.

The female parent of Waikiki was the cultivar identified as Pink Versicolor, an unpatented Hibiscus cultivar with single flower form and pink flower color with a red eye.

The male parent of Waikiki was the cultivar Fort Myers Yellow, an unpatented Hibiscus cultivar having single flower form and yellow flower color with an orange throat and a red eye.

Waikiki was discovered and selected as one flowering plant within the progeny of the stated cross by Frank C. Moser in August 1985, in ground beds in Alva, Fla.

The first act of asexual reproduction of Waikiki was accomplished when vegetative cuttings were taken from the initial selection in October 1985 in ground beds in Alva, Fla., by technicians working under the supervision of Frank C. Moser.

Horticultural examination of controlled flowerings of successive plantings has shown that the unique combination of characteristics as herein disclosed for Waikiki are firmly fixed and are retained through successive generations of asexual reproduction.

Waikiki has not been observed under all possible environmental conditions. The phenotype may vary significantly with variations in environment such as temperature, light intensity and daylength.

The following observations, measurements and comparisons describe plants grown in Alva, Fla. under greenhouse conditions which approximate those generally used in Florida for commercial potted Hibiscus production.

The following traits have been repeatedly observed and are determined to be basic characteristics of Waikiki, which, in combination, distinguish this Hibiscus as a new and distinct cultivar:

1. Pink Flower color with a dark red eye.
2. Regular single flower form, with flower diameter of 120 to 145 mm.
3. Excellent pot habit with vigorous growth, good branching and very uniform performance.
4. Flower life of a single day.

5. Easy to propagate.
6. Good resistance to Bacterial Leaf Spot (Pseudomonas sp.).
7. Good shipping tolerance (bud drop resistance).

The accompanying photographic drawings show typical plant habit, flower and leaf characteristics of Waikiki, with the colors being as nearly true as possible with illustrations of this type.

Sheet 1 is a color photograph of Waikiki grown as a commercially finished pot plant, with 4 cuttings in a 15 cm. pot.

Sheet 2 is a black and white photograph of the foliage of Waikiki, ranging from small or immature to relatively large and mature.

Of the commercial cultivars known to the inventor, the most similar in comparison to Waikiki is the female parent Pink Versicolor. Waikiki has a larger flower diameter, a lighter flower color and a more uniform performance when compared with Pink Versicolor. In addition, Waikiki has much better shipping tolerance (bud drop resistance) than Pink Versicolor, and is much more resistant to Bacterial Leaf Spot than Pink Versicolor, which is very susceptible.

It is worth noting that bud drop in shipping budded plants has been a severe problem in many Hibiscus cultivars currently being grown. Breeding for varieties not showing this trait is a high priority breeding objective. Therefore, the trait of bud drop resistance in Waikiki is very important. Resistance to Pseudomonas sp. (Bacterial Leaf Spot) is also a very important trait. Cultivars which are very susceptible to this disease cannot be grown successfully in the Florida environment.

In the following description color references are made to The Royal Horticultural Society Colour Chart. The color values were determined on May 18, 1990 in Salinas, Calif. on plant material grown in Alva, Fla. and shipped as a budded plant to Salinas, Calif., where it was flowered.

Classification:

*Botanical.*—*Hibiscus rosasinensis L.* cv Waikiki.
*Commercial.*—Greenhouse pot Hibiscus.

INFLORESCENCE

A. Flower (general):

*Size.*—120 to 145 mm.

*Borne.*—In axils of leaves, 1 per node.

*Form.*—Regular single.

*Life.*—One day.

*Blooming habit.*—Continuously, year round.

B. Corolla (petals):

*Color (general tonality from a distance of three meters).*—Pink.

*Color (upper surface).*—52C. Eye: Basal part of eye very dark red, closest to 53A to 53B, blending into 52C. Veins: Slightly darker than 52C, closest to 52B.

*Color (under surface).*—52D to 52C, veins 52C. Left ⅓ of underside of petal: Basal portion white, streaked with 52C; top portion slightly overlaid with 19B.

C. Reproductive organs:

*Androecium (stamens).*—Numerous anthers, abundant pollen; color 15A.

*Gynoecium (pistil).*—Stigma: 5 in number, rounded, hairy. Color: 46B. Style: Base closest to 53B, blending into 52C.

PLANT

A. General appearance:

*Height.*—20 to 25 cm. when grown as pot Hibiscus with 4 cuttings in a 15 cm. pot and 1 to 2 applications of 400 ppm CCC.

*Branching pattern.*—Semi-upright.

B. Foliage:

*Color (upper surface).*—147A.

*Color (under surface).*—147B.

*Shape.*—See photograph.

I claim:

1. A new and distinct Hibiscus plant named Waikiki, as described and illustrated.

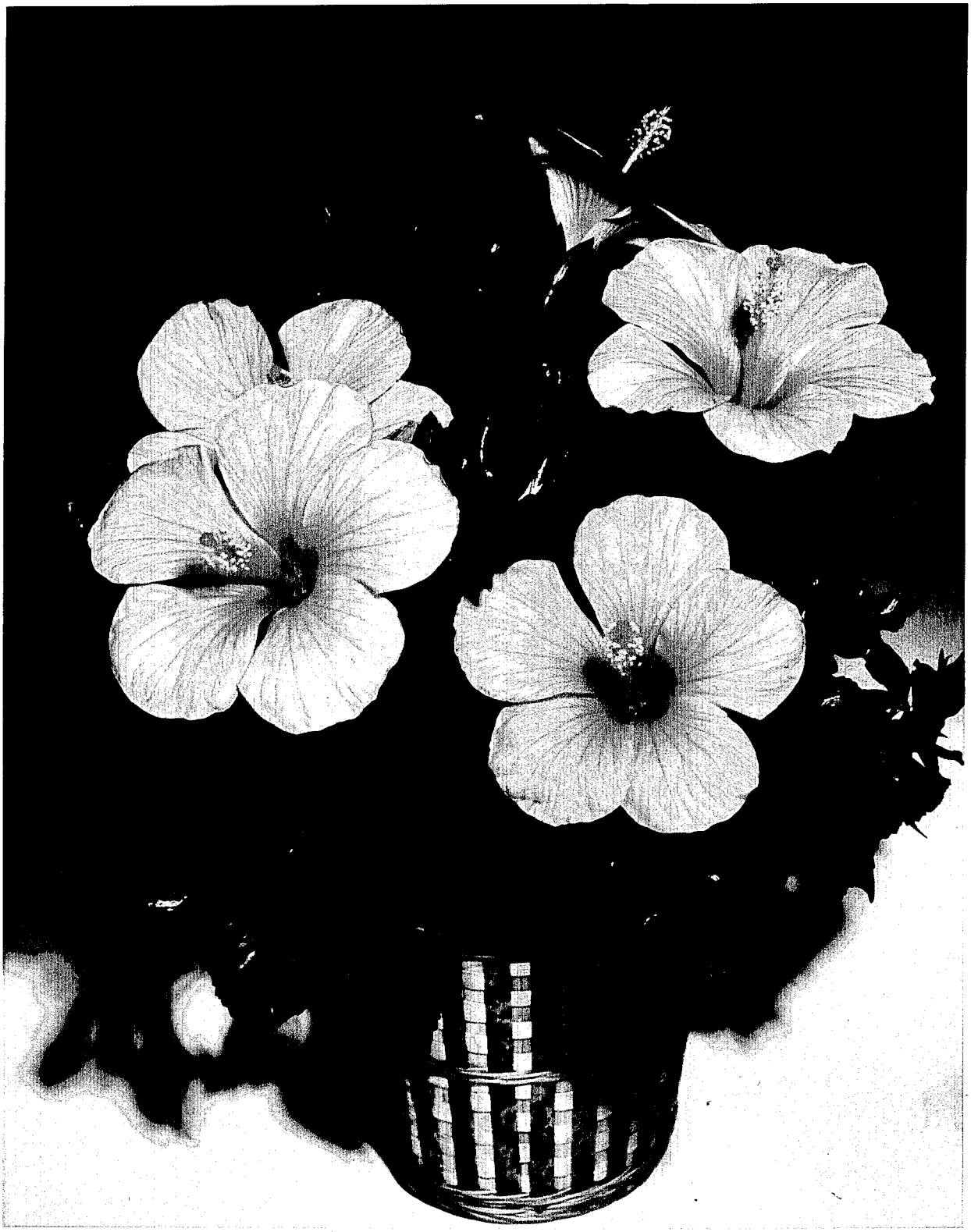

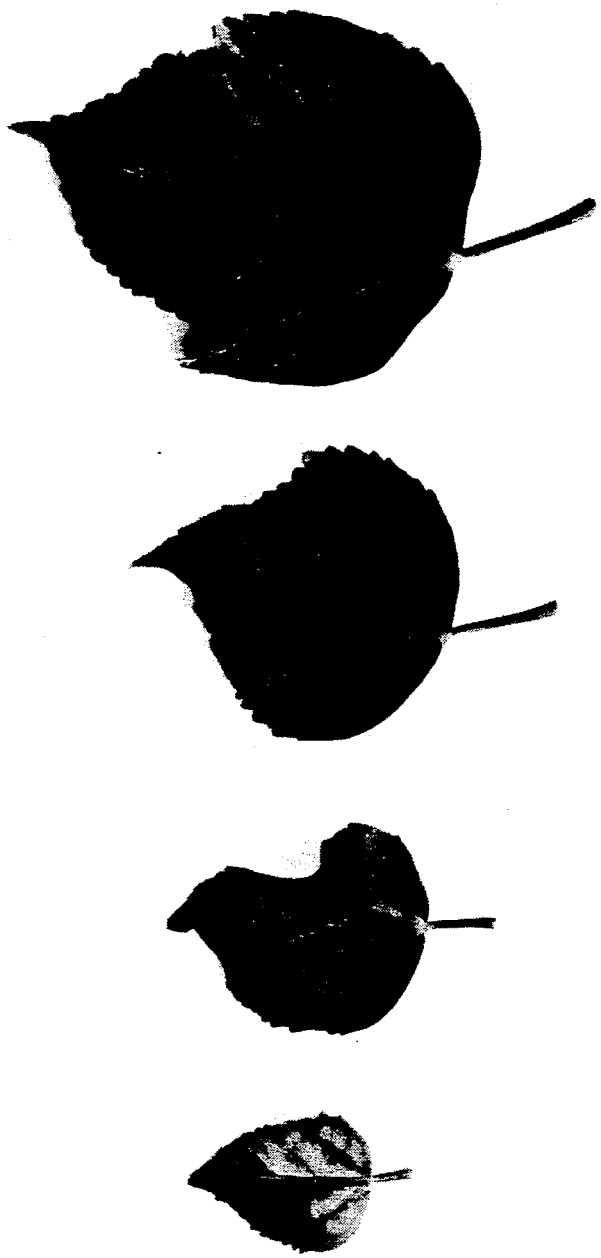

* * * * *